United States Patent [19]
Wichterle

[11] Patent Number: 4,971,732
[45] Date of Patent: Nov. 20, 1990

[54] METHOD OF MOLDING AN INTRAOCULAR LENS

[75] Inventor: Otto Wichterle, Prague, Czechoslovakia

[73] Assignee: Ceskoslovenska Academie Ved, Prague, Czechoslovakia

[21] Appl. No.: 244,598

[22] Filed: Sep. 13, 1988

Related U.S. Application Data

[63] Continuation of Ser. No. 23,909, Mar. 11, 1987, abandoned, which is a continuation of Ser. No. 898,750, Aug. 18, 1986, abandoned, which is a continuation of Ser. No. 613,714, May 16, 1984, abandoned.

[51] Int. Cl.$^5$ .............................................. B29D 11/00
[52] U.S. Cl. ..................................... 264/1.1; 264/1.7; 264/2.6; 425/808
[58] Field of Search .................. 264/1.1, 1.7, 2.2, 2.6; 425/808

[56] References Cited

U.S. PATENT DOCUMENTS

| | | | |
|---|---|---|---|
| Re. 27,401 | 6/1972 | Wichterle et al. | 523/106 |
| 2,834,023 | 5/1958 | Lieb | 3/13 |
| 3,674,504 | 7/1972 | Wichterle | 3/13 |
| 3,866,249 | 2/1975 | Flom | 623/6 |
| 3,965,063 | 6/1976 | Holcombe, Jr. | 523/106 |
| 4,163,608 | 8/1979 | Neefe | 3/13 |
| 4,347,198 | 8/1982 | Ohkada et al. | 264/2.6 |
| 4,379,864 | 4/1983 | Gallop et al. | 523/106 |
| 4,419,463 | 12/1983 | Atkinson et al. | 523/106 |
| 4,449,257 | 5/1984 | Koeniger | 623/6 |
| 4,452,776 | 5/1984 | Refojo | 523/106 |
| 4,573,998 | 3/1986 | Mazzocco | 623/6 |

OTHER PUBLICATIONS

Binder, P. S. et al.; "Hydrogel Keratophakia in Non-Human Primates", Current Eye Research, vol. 2, No. 7, 1982/1983, pp. 535–542.

Binder, P. S., "Hydrogel Implants for the Correction of Myopia", Current Eye Research, vol. 2, No. 7, 1982/1983, pp. 435–441.

Binder, P. S. et al.; Hydrogel Refractive Keratoplasty. Lens Removal, and Exchanges, Cornea; vol. 2, No. 2, 1983, pp. 119–125.

Binder, P. S. et al., "Hydrophilic Lenses for Refractive Keratoplasty: The Use of Factory Lathed Materials", Contact Lens Assoc. of Ophthalmologists Journal, Jan. 1984, pp. 105–111.

Primary Examiner—James Lowe

[57] ABSTRACT

An improved intraocular lens, methods of fabricating the same, and methods of implantation of the intraocular lens in a human eye. The intraocular lens implant is a hydrogel and has an index of refraction approximating the refractive index of the natural crystalline lens of the human eye. Fabrication of the intraocular lens is effected in an open concave mold which has a sharp, well-defined peripheral mold edge. The intraocular lens is implanted in the posterior chamber after the cataract operation.

19 Claims, 1 Drawing Sheet

METHOD OF MOLDING AN INTRAOCULAR LENS

This application is a division of application Ser. No. 023,909 filed Mar. 11, 1987, now abandoned, which in turn is a continuation of application 898,750 filed Aug. 18, 1986, now abandoned, which in turn is a continuation of application 610,714 filed May 16, 1984, now abandoned.

BACKGROUND OF THE INVENTION

1. Field of the Invention

This invention relates to intraocular lenses of hydrogel material adapted for implantation in a human eye.

2. Discussion of the Prior Art

The concept of the use of intraocular lenses for the correction of aphakia has a long history. Much of the pioneering work was performed by Harold Ridley in London and by Binkhorst in the Netherlands. A comprehensive history of the development and results of the intraocular implant lens is presented by a thesis by Marcel Eugene Nordlohne and reproduced in Documenta Ophthalmologica, Vol. 38, Issue 1, Dec. 16, 1974.

A summary of the history of various artificial lens implants is also found in an article written by D. P. Choyce, published in the Annals of Ophthalmology, October, 1973, pages 1113–1120. In most cases lenses were made from organic high polymers such as, for example, poly(methyl methacrylate). It has also been proposed to implant glass lenses and to utilize lenses made of pure silicate glass. Specific glass compositions have been proposed in the disclosure of U.S. Pat. No. 3,996,627, for example. Although glasses have certain advantages as ocular implants, they are, in most cases, of a density rendering finished lenses relatively high in weight and less than optimum in this respect as implants. An early report by Schiferli in 1795 described an attempt by Casaamata to introduce a glass lens into the eye after a cataract operation. The lens immediately slipped back toward the fundus of the eye.

Many patents are addressed to the problem of mounting the intraocular lens within the eye so that it can perform its intended function with a minimum of trauma to the eye; see for example U.S. Pat. Nos. 2,834,023; 3,711,870; 3,673,616; 3,866,249; 3,906,511; and 3,913,148.

Intracameral lenses, i.e., prosthesis for the removed natural lens, fabricated of poly(methyl methacrylate) or of many glass-like materials generally are characterized by a refractive index value which is substantially greater than the refractive index value of 1.396 of the natural crystalline lens of a human eye. For example, intraocular lenses of the poly(methyl methacrylate) type possess a refractive index in the area of 1.53. Thus, the geometry and shape of an intraocular implant lens of the poly(methyl methacrylate) type differ from that of a natural lens to enable the artificial lens immersed in the refracting medium (the aqueous humor and vitreous humor) to substantially duplicate the refractive index characteristic of the natural lens. For example, the artificial lens is shaped with substantially smaller curvatures of both optical surfaces than is the case with the natural lens. However, such changes in shape of the artificial lens precludes implantation in the exact position of the space occupied by the natural lens. Further disparity is noted in the specific weights of conventional material, e.g., about 1.25, used in the fabrication of intraocular lenses compared with the specific weight of the natural lens (about 1.1). Thus an IOL implant of conventional material immersed in the refracting medium of the eye appears several times heavier than the natural lens. This disadvantage has been diminished by the recent practice of designing thin intracameral lenses which, however, further increases the diversity of shape between the artificial lens and the natural lens.

Many adaptations have been proposed, and several actually used, to hold a miniaturized but relatively heavy intraocular lens system (body and mounting or securing means) in the desired optical zone. Pat. No. 4,073,015 discloses the mounting and securing of an intraocular lens so as to hold it in place permanently without lasting irritation to the patient. The patentees state that the lens is made of acrylic, hydrogel, or other biologically tolerable lens material and is formed with laterally extending planar flanges or haptical portions. A woven or knitted fibrous material, such as Dacron, is attached to the outer perimeter of the haptical portions and provide sites into which tissue of the iris can grow so as to form a permanent anchor for the lens; see column 1, line 66 to column 2, line 7 of U.S. Pat. No. 4,073,015. The intraocular lens structure and lens mounting system (lens body, integral haptical portion, loops, etc.) is inserted into the location previously occupied by the crystalline lens by expanding the pupillary opening of the iris to admit the said system; column 3, lines 56–66 of U.S. Pat. No. 4,073,015. It is apparent from the specification and drawings that the lens body of the patentees' intraocular lens system is significantly smaller than the natural lens of the patient's eye.

SUMMARY OF THE INVENTION

The present invention alleviates and/or substantially eliminates many of the problems associated with the implantation of an intraocular lens (IOL) into the general location previously occupied by the natural crystalline lens. The IOL can be inserted into the empty space after surgical extraction of the cloudy or opacified natural lens by relatively simple means. The IOL body substantially fills or occupies the chamber of the extracted natural lens thereby oftentimes substantially decreasing or even eliminating in some instances the need for lens fastening and positioning means. The IOL hydrogel material possesses or approximates many of the characteristics of a natural crystalline lens including, among other significant properties, an index of refraction value approximating 1.4. The IOL can be fabricated, for example, by techniques using inexpensive open molds of predetermined dimensions. The involved process proceeds smoothly and is economically attractive. Also, technically, the IOL can be shaped by means of mechanical cutting, e.g., turning, grinding and/or polishing, the generally anhydrous form of the water-swellable, water-insoluble, highly hydrophilic material (known in the art as a xerogel which is hydratable to the hydrogel).

Accordingly, it is an object of the invention to provide improved intraocular implant lenses of hydrogel materials which are stable, biologically inert, biocompatible with living tissue, and possessing suitable refractive indices.

It is another object of the invention to provide improved processes and apparatus for fabricating intraocular lenses via simple, inexpensive mold casting techniques.

It is a further object of the invention to provide unique means for introducing hydrogel intraocular lenses into the desired chamber of a human eye.

A still further object of the invention is to provide an improved intraocular lens body having, if necessary, unique circumferential thread-like means within and proximate to the surface of the IOL body per se which serve to anchor or secure the IOL body in a fixed position in a human eye.

A further object of the invention is to provide a human eye with a hydrogel intraocular implant lens of hydrogel material generally located in the space formerly occupied by the removed natural lens.

These and other objects will become readily apparent from a consideration of this disclosure.

DETAILED DESCRIPTION OF THE INVENTION

This invention pertains to a novel stable intraocular lens body of hydrogel material useful as implants for the natural crystalline lens of a human eye removed by surgical means or otherwise. The intraocular hydrogel lens body has a shape substantially defined by two rotationally symmetrical and coaxial optically finished surfaces, at least one surface being convex, e.g., double-convex (preferred), plano-convex, and slightly concavoconvex, provided the required focal length is obtained. In a preferred form both surfaces, e.g., double-convex, of the lens body have a continuous transition, i.e., without sharp edges or sharp line of demarcation. The intraocular lens consists essentially of a water-swellable, water-insoluble, stable hydrogel which contains at least about 60% by weight, preferably at least about 65–70% by weight of water or physiologic saline (about 0.9% by weight saline solution) based on the total weight of the hydrogel. The hydrogel, in osmotic equilibrium with physiologic saline, possesses an index of refraction of about 1.4, desirably from about 1.37 to about 1.45, preferably from about 1.38 to about 1.42, and preferably still from about 1.39 to about 1.41. The upper limit of water content in the hydrogel is controlled by its ability to be generally shape-retaining with sufficient mechanical strength to function as an artificial lens body replacement for the opacified natural lens. In general, an upper water content limit of 90–95% by weight is suitable; 85–90% by weight is desirable in various embodiments. Hydrogels made via polymerization processes are preferred, and in this respect, the concentration and starting material(s) of choice, e.g., monomer(s), will significantly influence the water-swellability characteristic of the resulting polymer(s).

The hydrogel material, in the shape of the intraocular implant lens, is further characterized by the following properties: transparency, good optics (giving it capability to function as an IOL), biologically inert, biocompatibility with living tissue, stability in normal physiologic medium, good mechanical properties such as softness, elasticity and modulus. The hydrogel material can be derived from synthetic or natural stable materials, or modification of both types, e.g., the various types of modified collagens and other natural products, polymerization products from ethylenically unsaturated polymerizable monomers, products from the condensation reaction of polyisocyanates and polyols (natural and synthetic), and the like. In a preferred form the hydrogel is a synthetically derived material.

Figure 2:
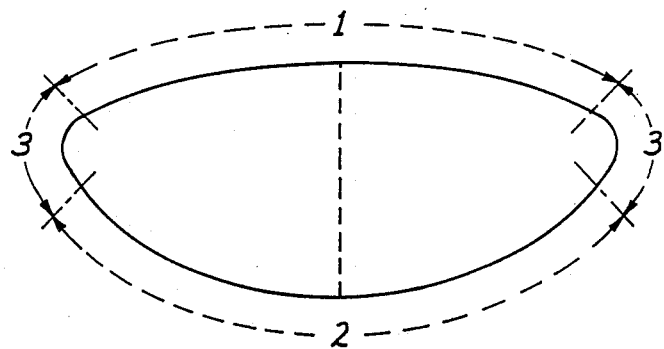
FIG. 2 is a cross-sectional side view of the intraocular hydrogel lens as separated from mold 10. Curves 1 and 2 of this view of the IOL are in agreement with the curves defined by mold cavity side section 7 and convex meniscus side section 11 (FIG. 1).

The general shape of the novel intracameral hydrogel lens approximates the general shape of the natural crystalline lens in the capsula lentis. Referring to FIG. 2, the artificial lens (preferred) is characterized by a front surface 1 whose general shape resembles a flat ellipsoid having a central radius of curvature in the range of from about 7.5 to about 15 mm; a back surface 2 which is a spherical surface or a rotationally symmetrical surface of the second order, the central radius of curvature being in the range of from about 5 to 8 mm; two toroidal surfaces 3 delineated by front surface 1 and back surface 2 and having the shape of a common torus; and a central lens thickness (between front surface 1 and back surface 2) of from about 2.5 to about 5 mm.

In one aspect of the invention suitable intraocular lenses can be fabricated from starting materials which are employed in the manufacture of so-called soft hydrophilic contact lens of high water content and other articles of similar hydrogel materials. Desirably the hydrogel is characterized by a relatively slightly to moderately crosslinked polymeric network and such products are well described in the literature. The operative conditions necessary to effect the appropriate reaction, especially the polymerization reaction, are of course well known in the art; see by way of illustrations U.S. Pat. Nos. 4,032,599; 4,067,839; 4,036,814; 4,095,877; 4,275,183; 4,361,689; 4,388,436; and 4,408,023. To the extent appropriate, the foregoing patents are hereby incorporated by reference into this disclosure as if set out in full text.

One of ordinary skill in the art can select the monomer or mixture of monomers of choice, including the appropriate crosslinking means, catalyst(s), solvent, and the like. Illustrative reactants include hydrophilic monomers such as 2-hydroxyethyl methacrylate, glycidyl methacrylate, N-vinylpyrrolidone, methacrylamide, acrylamide, N-methylacrylamide, methacrylonitrile,-diethylene glycol monomethacrylate, alkali metal salts of itaconic acid, of methacrylic acid, and the like. The hydrophilicity of the polymeric product can oftentimes be enhanced by using, for example, methacrylic acid as one of the monomers.

Crosslinking means include, for example, di- or polyfunctional species such ad divinylbenzens, ethylene glycol diacrylate or dimethacryate, propylene glycol diacrylate or dimethacrylate, and the polyacrylate or polymethacrylate esters of the following polyols: triethanolamine, glycerol, diethylene glycol, triethylene glycol, tetraethylene glycol, trimethylolpropane, and the like. Other crosslinking monomers can be illustrated by N,N-methylene-bis-acrylamide or methacrylamide and sulfonated divinylbenzene. Polymerization can also be effected using, for example, radiation (U.V., X-Ray, microwave, or other well-known forms of radiation) with/without the presence of well-known initiator(s) and/or catalyst(s) such as the organic peroxides, the alkyl percarbonates, hydrogen peroxides, and inorganic materials such as ammonium, sodium, or potassium persulfate. Polymerization temperatures can vary from about 20° C., and lower, to about 100° C., and higher. Desirably the polymerization of the ethylenically unsaturated compounds is carried out in the presence of a liquid medium and/or plasticizer and/or solvent, e.g., water, glycerol, miscible organic liquid/ water media, and the like.

Mixtures of reactants are generally preferred since hydrogels having "tailor-made" characteristics can be prepared. Mixtures of hydrophilic and hydrophobic rectants in appropriate concentrations can be utilized providing the resulting polymeric product has the capability of meeting the desired water content level illustrated previously. Illustrative hydrophobic monomers include the lower alkyl methacrylates such as methyl methacrylate.

The foregoing discussion is well documented in the literature, especially the body of patent literature relating to so-called soft contact lenses.

In one aspect the invention is directed to a novel method of preparing the novel intraocular lenses via casting a liquid mixture comprising lens-forming reactant(s) and other ingredients, e.g., water (preferred) and/or miscible organic liquid/water (preferred) or organic medium such as glycerol (preferred) desirably into an open concave mold. The mold is fabricated from any suitable material which forms with the said mixture a wetting angle greater than zero. The concave mold cavity has the shape of a sphere or rotational symmetrical surface of second order and terminates with a horizontal circular sharp edge. The liquid mixture of monomer(s) is dosed into the mold cavity in a predetermined amount which generally exceeds (preferred) the volume of the cavity defined by the circular sharp edge. The liquid mixture does not flow over the circular edge, but forms a convex surface of the type of a flat rotational ellipsoid above the circular edge. In this manner the desired surfaces of the intraocular lens are formed in situ. In this procedure the wetting angle, as indicated above, is greater than zero. In other words, if the surface is unwettable (e.g., Teflon (polytetrafluoroethylene) or is not completely wetted, the liquid mixture in excess of the volume of the mold cavity does not spill over, but rather it forms the convex menisci side sections shown as 11, 12, 13 and 14 in FIG. 1. The larger the wetting angle the greater the amount of overdosing that can be tolerated. Of course, a point is reached where surface tension, adhesive forces, and other forces and attractions cannot hold the volume of liquid mixture within the bulging convex surface above the circular mold edge. A most suitable shape of the projecting meniscus of liquid mixture is achieved with dosed volumes (of liquid) which are about 10 to about 80 volume percent greater than the volume of the mold cavity per se (below sharp horizontal edge 5). An arbitrary central radius therefore can be obtained by adjustment of the amount of liquid overdosed above the volume of the mold cavity. One embodiment of the invention, as indicated previously, includes an IOL which can have a plano and even a slightly concave front surface. In such instances the dosing of mold cavity 4 with liquid mixture may slightly exceed sharp circular mold edge 5, may be level with mold edge 5, or may even be slightly below mold edge 5, depending on the IOL optics required by the patient. Preferably, the liquid mixture comprising monomer(s) is introduced into the cavity in an amount at least sufficient to approximatley reach the level of the shape edge. The liquid mixture comprising monomer(s) after dosing is subjected to polymerization conditions, e.g., polymerization temperature in an inert atmosphere or it is exposed to a photochemically effective light, if photoinitiators are used. On completion of the polymerization reaction, the molded product may be removed from the mold or the mold and product can be immersed in water where it (IOL product) is readily released from the mold after swelling. The IOL product does not require any additional mechanical treatment because its surface is optically precise and completely smooth. It needs only removal of extractable low-molecular weight impurities by required washings with water or aqueous alcohol and the final equilibration with physiological saline. Thereafter it can be sterilized and stored until used for the intended purpose. The intraocular lens of the invention can also be manufactured from a strongly hydrophilic material in the anhydrous or almost anhydrous state (xerogel), by mechanical processing (turning, grinding and polishing) to the required shape but on a reduced scale, followed by the subsequent swelling in aqueous medium of the anhydrous IOL replica to the required size. This method, being somewhat more costly (labor-intensive), is not as desirable as the casting technique described previously.

In view of the soft and elastic shape retaining nature of the novel intraocular lens, the lens can be conveniently sterilized and stored, preferably in a tubular container, and thus made ready for use during primary (preferred) or secondary implantation operations. In one form the tubular container (e.g., fabricated of flexible plastic such as polyethylene) has a diameter at one end thereof which is smaller than the diameter (thickness) of the intraocular lens. The IOL can be forced to the narrower end of a flexible, thin walled container by exerting pressure on the container to cause the IOL to become sufficiently deformed, oblong-wise, so as to be capable of exiting from the narrow opening of the container. Pressure on the container can be conveniently effected by hand pressing the container (e.g., by the ophthalmologist) to the extent necessary to cause the deformation but not the rupture or loss of integrity of the intraocular lens. In amoeba-like fashion the IOL is thus squeezed out from its container and will thereafter readily assume its original size and shape. If the internal wall of a container, conveniently a flexible container such as plastic, e.g., polyethylene or polypropylene, is hydrophilized as by techniques known in the art, the movement of the IOL therein and its exit therefrom can be made quite facile. The intraocular lens may be fixed within the container in a manner whereby the front and back surfaces of the IOL are indicated on the container wall.

A further aspect of the invention provides a novel method of inserting the novel IOL body into the empty space created, for example, by the surgical extraction of a turbid lens. If the rear capsula lentis has not been removed it can function as a thin natural membrane or foil which as a rule is clear and which precisely delimits the space for an artificial lens of similar size and shape. The most closely fitting intraocular lens can be generally ascertained according to the shape and volume or weight of the removed natural lens. In this respect the ophthalmologist can choose from a large stock of the novel intracameral lenses and insert the appropriate lens into the space occupied by the removed lens. If the capsula lentis is intact after the removal of the turbid lens and if the ciliary muscles proximal thereto have not degenerated, the novel IOL, being sufficiently soft and elastic and occupying the space formerly occupied by the natural lens, can be at least partially deformed by the muscles (as in the functioning of a normal natural lens) thereby imparting at least partial accommodation to the eye of the patient.

The hydrated IOL can be introduced into the posterior chamber of the eye (utilizing a tubular container of the principle discussed previously) as through the pupillary aperture which is smaller than the diameter of the IOL in it normal relaxed state or through any small acceptable surgical opening to the posterior chamber. In view of the capability of the intraocular lens to become temporarily deformable into amoeba-like shapes, the surgical opening for introducing the novel IOL into the empty chamber by the novel techniques illustrated previously can be of the order of 1 to 2 mm (and greater if required). In principle, the IOL can be inserted through the pupillary aperture in a partially or essentially dry state (since the lens dimensions are measurably smaller in such state). Such lens assumes its final dimensions after several hours in the eye by swelling to equilibrium in the surrounding vitreum.

In the event the IOL will not maintain its correct position in the human eye, the IOL can be provided with a thread-like mounting means such as textile fibrous material, e.g., Dacron and/or absorbable surgical material, advantageously in a ring-like arrangement about the IOL circumference. Such means should provide maximum non-interference with the optical zone of the intraocular lens. The novel casting polymerization technique can take place in the presence of, for instance, a preshaped reinforcing (e.g., thread-like or filament-shaped) structure, crimped if desired, to provide stretch and elongation characteristics, contained within the concave mold cavity proximate to the shaped edge of the mold perimeter. In its preferred form the resulting IOL lens product possesses an optical zone essentially free from interference of the mounting means thus imbedded therein. Such mounting means can be anchored within the eye, e.g., iris, by known surgical procedures. In one embodiment the mounting means may comprise thread-like or fine knit-like material which extends outwardly from the lens body (preferably proximal to toroidal surface 3). Such material, textile and/or absorbable suture, engage eye tissue proximal thereto, and with the passage of time an intermingling of tissue growth with the said material takes place. The non-absorbable thread-like material will be permanently engaged with the tissue growth; the absorbable thread-like material is, as expected, absorbed into the tissue body. The anchoring technique of the intraocular lens in the above manner is effective and permanent with minimum trauma to the eye. However, as stated previously, it may not be necessary to secure the IOL implant by surgical means. If the IOL is properly chosen in shape and size and is properly inserted into the posterior chamber, especially in those cases where the rear surface of the capsula lentis is not destroyed, the prognosis of a permanent IOL implant is favorable.

EXAMPLES 1-4

A solution is prepared using 10 ml of 2-hydroxyethyl methacrylate, 0.03 ml of ethylene glycol dimethacrylate, 0.16 g of sodium methacrylate, and 10 ml of glycerol. To this solution there is added 0.015 g of ammonium peroxodisulfate in the form of a 25% aqueous solution as a polymerization catalyst. The resulting clear liquid is charged into the concave cavity of four separate polypropylene molds shown in FIG. 1, the cavity of which is formed from a central spherical cap of a sphere radius 6 mm and width 9 mm continuously linked to a toroidal surface. The toroidal surface is formed by the rotation of a meridian circle of diameter 1 mm, the center of which is distanced from the axis 3.7 mm. The toroidal surface is terminated by a sharp circular edge of diameter 9.4 mm which delimits the sagittal depth of mold equal to 2.9 mm. The cavity volume of this mold is 134 microliters.

The volume of clear polymerizable liquid separately dosed into each of the four molds was 181, 214, 247, and 278 microliters, respectively. The resulting convex menisci surfaces of the dosed molds, for convenience, are shown as 11, 12, 13, and 14 of FIG. 1. The molds are maintained in a horizontal position at all times and are carefully inserted into a tunnel heated to 75° C. with an inert atmosphere maintained by a moderate stream of nitrogen. Practically complete conversion is achieved after 30 minutes of polymerization. The molds with gel moldings are immersed in distilled water at ambient temperature for 24 hours. The lenses are then released from the molds. To obtain perfect washing, the molded lenses are heated for several days to 80° C. in 50% aqueous isopropyl alcohol (fresh aqueous isopropyl alcohol is used daily). Similar washings are carried out with distilled water for several days and the washed lenses are eventually stored in an aqueous solution containing 0.6% NaCl and 0.43% NaHCO$_3$ in a form ready for surgical application. The intraocular lenses made from the above stated four various doses of liquid mixture have the characteristics set out in Table I below:

TABLE I

| IOL | THICKNESS (mm) | CENTRAL CURVATURE (mm)[a] | REFRACTION (diopters)[b] | REFRACTIVE INDEX | DIAMETER (mm) |
|---|---|---|---|---|---|
| 1 | 4.1 | 15 | 13 | 1.41 | 9.7 |
| 2 | 4.9 | 10 | 15 | 1.41 | 9.7 |
| 3 | 5.6 | 8 | 16.5 | 1.41 | 9.7 |
| 4 | 6.3 | 7 | 18 | 1.41 | 9.7 |

[a] Central curvature of front surface.
[b] Refraction in immersion of physiologic saline.

Figure 1:
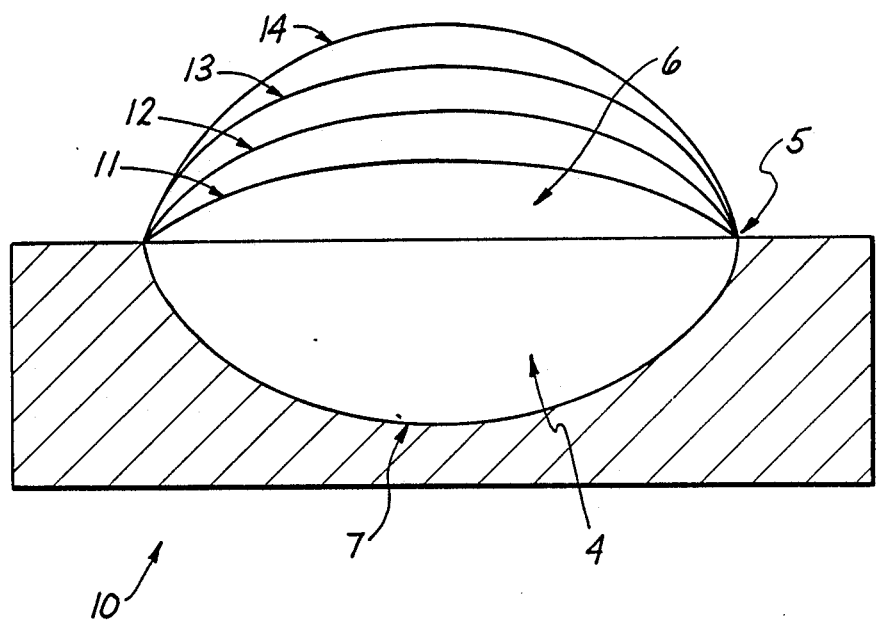
FIG. 1 is a cross-sectional side view of concave mold 10 with curves 11, 12, 13 and 14 representing side sections through the surface of convex menisci formed by overdosing mold cavity 4 with liquid comprising polymerizable reactants.

FIG. 1 shows the axial sectional view in which the front surface of the four intraocular lenses corresponds to the curves defined by 11, 12, 13, and 14.

If the polymerizable liquid mixture is prepared by diluting the above stated amount of monomers with a volume of glycerol other than 10 ml, there is obtained an intraocular lens having the same shape but of different size. The size differs from the original IOL size by a factor $f=(0.4+0.04V)^{-\frac{1}{3}}$, wherein V is the amount of added glycerol in ml. Thus, by diluting the monomer mixture with only 7 ml of glycerol, dimensions, i.e., diameter, thickness, and radii of curvature, will be increased by the factor 1.14. On the other hand, by diluting with 20 ml of glycerol, the IOL lenses will be contracted by the factor 0.94. Because dilution of the monomer mixture does not substantially affect the resulting refractive index of gel, the refraction is changed so, that the above given values should be divided by the pertinent factor f.

Other lightly crosslinked hydrophilic polymers, desirably those which have a refractive index between about 1.38 and 1.44 in equilibrium with the physiologic medium, can be used similarly as the aforesaid type of gel.

What is claimed is:

1. A process for fabricating an intraocular lens which comprises:
    a. introducing a liquid mixture comprising intraocular lens-forming reactants into a cavity of a mold which has a concave surface substantially corresponding to the convex shape of one convex surface of an intraocular lens product, said cavity having an inner wall and said mold having an upper surface adjacent said cavity which meets said inner wall at a sharp edge;
    b. said liquid mixture being introduced in an amount at least sufficient to approximately reach the level of said sharp edge;
    c. reacting the lens-forming reactants for a period of time sufficient to form said intraocular lens product having said one convex surface and another convex or plano surface substantially opposed to said one convex surface;
    d. equilibrating said intraocular lens product by washing said intraocular lens product in an aqueous medium to form a washed intraocular lens product; and thereafter
    e. storing and maintaining said washed intraocular lens product, having at least one optically finished convex surface, in osmotic equilibrium with physiologic solution.

2. The process of claim 1 wherein said liquid mixture comprises polymerizable ethylenically unsaturated compound.

3. The process of claim 2 wherein the wetting angle between said mold and said liquid mixture is greater than zero and said liquid mixture is introduced into said cavity in a predetermined amount which exceeds the volume of said cavity and thereby forms above said sharp edge a convex body of said liquid mixture bounded by said sharp edge; and wherein said washed intraocular lens product has two convex surfaces.

4. The process of claim 3 wherein said reacting occurs in the presence of a lens mounting means which extends outwardly from said sharp edge, and said washed intraocular lens product includes said lens mounting means essentially free from interference with an optical zone of said washed intraocular lens product.

5. The process of claim 2 wherein said liquid mixture comprises 2-hydroxyethyl methacrylate.

6. The process of claim 2 wherein said reacting occurs in the presence of a lens mounting means which extends outwardly from said sharp edge thereby embedding said lens mounting means in said intraocular lens product.

7. A process for fabricating an intraocular lens which comprises:
    a. introducing a liquid mixture comprising intraocular lens-forming reactants into a cavity of a mold which has a concave surface substantially corresponding to the convex shape of one surface of the intraocular lens product to be formed, said cavity having an inner wall and said mold having an upper surface adjacent said cavity which meets said inner wall at a sharp edge;
    b. said liquid mixture being introduced in an amount at least sufficient to approximately reach the level of said sharp edge;
    c. maintaining the entire amount of said liquid mixture introduced into said cavity without overflowing said sharp edge; and
    d. reacting the lens-forming reactants for a period of time sufficient to form an intraocular lens product having at least one convex surface.

8. The process of claim 7 which further comprises:
    e. washing said intraocular lens product in an aqueous medium to form a washed intraocular lens product; and
    f. thereafter storing and maintaining said washed intraocular lens product, having at least one optically finished convex surface, in osmortic equilibrium with physiologic solution.

9. The process of claim 8 wherein said reacting occurs in the presence of a lens mounting means which extends outwardly from said sharp edge, 10. The process of claim 7 wherein said liquid mixture comprises polymerizable ethylenically unsaturated compound.

11. The process of claim 7 wherein the wetting angle between said mold and said liquid mixture is greater than zero and said liquid mixture is introduced into said cavity in a predetermined amount which exceeds the volume of said cavity and thereby forms above said sharp edge a convext body of said liquid mixture bounded by said sharp edge; and wherein said intraocular lens product has two convex surfaces.

12. The process of claim 11 wherein said reacting occurs in the presence of a lens mounting means which extends outwardly from said sharp edge, thereby embedding said lens mounting means in said intraocular lens product.

13. The process of claim 7 wherein said liquid mixture comprises 2-hydroxyethylmethacrylate.

14. The process of claim 7 wherein said reacting occurs in the presence of a lens mounting means which extends outwardly from said sharp edge, thereby embedding said lens mounting means in said intraocular lens product.

15. A process for fabricating an intraocular lens which comprises:
    a. introducing a liquid mixture comprising intraocular lens-forming reactants into a cavity of a mold which has a concave surface substantially corresponding to the convex shape of one convex surface of the intraocular lens product to be formed, said cavity having an inner wall and said mold having an upper surface adjacent said cavity which meets said inner wall at a sharp edge;
    b. said liquid mixture being introduced in an amount at least sufficient to approximately reach the level of said sharp edge; and
    c. reacting the lens-forming reactants for a period of time sufficient to form an intraocular lens product having said one convex surface and another convex or plano surface substantially opposed to said one convex surface. and said washed intraocular lens product includes said lens mounting means essentially free from interference with an optical zone of said washed intraocular lens product.

16. The process of claim 15 wherein said liquid mixture comprises polymerizable ethylenically unsaturated compound.

17. The process of claim 15 wherein the wetting angle between said mold and said liquid mixture is greater than zero and said liquid mixture is introduced into said cavity in a predetermined amount which exceeds the volume of said cavity and thereby forms above said sharp edge a convex body of said liquid mixture bounded by said sharp edge; and wherein said intraocular lens product has two convex surfaces.

18. The process of claim 15 wherein said liquid mixture comprises 2-hydroxyethylmethacrylate.

19. The process of claim 15 wherein said reacting occurs in the presence of a lens mounting means which extends outwardly from said sharp edge, thereby embedding said lens mounting means in said intraocular lens product.

* * * * *